United States Patent [19]
Hantzer et al.

[11] Patent Number: 5,811,624
[45] Date of Patent: Sep. 22, 1998

[54] SELECTIVE OPENING OF FIVE AND SIX MEMBERED RINGS

[75] Inventors: Sylvain Hantzer; Michele S. Touvelle, both of Baton Rouge, La.; Jingguang G. Chen, Somerville, N.J.

[73] Assignee: Exxon Research and Engineering Company, Florham Park, N.J.

[21] Appl. No.: 524,358

[22] Filed: Sep. 5, 1995

[51] Int. Cl.$^6$ .................................. C07C 2/00; C07C 2/58

[52] U.S. Cl. .......................................... 585/700; 585/721

[58] Field of Search ................... 585/700, 708, 585/709, 713, 721; 502/174, 177, 200

[56] References Cited

U.S. PATENT DOCUMENTS

5,345,026  9/1994  Chang et al. ............................ 585/700

*Primary Examiner*—Gary P. Straub
*Assistant Examiner*—Tanaga Boozer
*Attorney, Agent, or Firm*—Henry E. Naylor

[57] ABSTRACT

A process for opening $C_5$ and $C_6$ rings without substantial cracking. A feedstream containing compounds comprised of at least one $C_5$-ring, at least one $C_6$-ring, or both, is contacted, in the presence of hydrogen, with a transition metal catalyst selected from the group consisting of carbides, nitrides, oxycarbides, oxynitrides, and oxycarbonitrides. The transition metal is selected from the group consisting of metals from Groups IVa, Va, and VIa of the Periodic Table of the Elements.

10 Claims, 3 Drawing Sheets

—— Ethyl cyclopentane (EtCP)

·········· 1,1-dimethyl cyclopentane (1,1-DMCP)

- - - - - 1,2-dimethyl cyclopentane (1,2-DMCP)

— - - 1,3-dimethyl cyclopentane (1,3-DMCP)

SELECTIVE OPENING OF FIVE AND SIX MEMBERED RINGS

FIELD OF THE INVENTION

The present invention relates to a process for opening $C_5$ and $C_6$ rings without substantial cracking. A feedstream containing compounds comprised of at least one $C_5$-ring, at least one $C_6$-ring, or both, is contacted, in the presence of hydrogen, with a transition metal catalyst selected from the group consisting of carbides, nitrides, oxycarbides, oxynitrides, and oxycarbonitrides. The transition metal is selected from the group consisting of metals from Groups IVa, Va, and VIa of the Periodic Table of the Elements.

BACKGROUND OF THE INVENTION

There is an increasing demand for environmentally friendly hydrocarbons and clean-burning high performance fuels, such as distillate fuels like diesel and jet fuels. Distillate fuels typically contain paraffins, naphthenes, and aromatics. For fuel quality parameters such as cetane, gravity and emissions, paraffins are the most desirable components, followed by naphthenes, followed by aromatics. The least desirable are multi-ring aromatic compounds. While various refinery processes produce distillate fuels, these processes are typically limited in their capability to produce high quality distillate fuel and/or high yields of distillate fuel. For example, conventional hydrogenation processes saturate aromatic rings to naphthenes, thereby increasing the cetane number, and increasing the API gravity (lower density). The disadvantage of hydrogenation alone is that naphthenes have generally lower cetane values and are more dense than paraffins having substantially the same number of carbon atoms. The greater density of naphthenes results in reduced volume of the distillate fuel blend relative to a composition containing similar concentrations of paraffins instead of naphthenes. Similarly, multi-ring naphthenes are generally more dense and have lower cetane values than single-ring naphthenes having substantially the same number of carbon atoms. In addition, naphthenes can be converted to aromatics via oxidation reactions. Since combustion of naphthenes in fuels occurs under oxidizing conditions, there is the potential for naphthenes to revert to aromatics under combustion conditions, thus further reducing fuel quality and increasing emissions of undesirable components.

Another conventional refinery process for producing distillate fuels is hydrocracking. Hydrocracking catalysts are typically composed of hydrogenation metals supported on acidic supports, such as zeolites. These catalysts are effective, under typical process conditions, for extensive hydrogenation of aromatics and for reducing the number of ring structures, however with the accompanying liability of extensive cracking to lower boiling products including gases which lowers the overall boiling range and limits the volume of final distillate product. In fact, analyses of distillate boiling range paraffin content in hydrocracking feeds versus products suggest little net increase in production of these paraffins via hydrocracking, rather concentration of paraffins in the final product through the cracking of ring structures to lower molecular weight compounds which no longer reside in the distillate boiling range. Thus, the apparent increase in distillate boiling range paraffins and improved distillate fuel quality can result primarily from a combination of hydrogenation of aromatics and a concentration of paraffins in a reduced volume of distillate product.

There is also an increasing demand for low toxicity, biodegradable solvents, of which paraffins are a preferred class. Consequently, it is desirable to reduce the cyclic compound content of hydrocarbon solvent blends, in general, and to convert naphthenes to paraffins, in particular. While there are descriptions of ring opening reactions in the prior art, owing to the increasing demand for more environmentally friendly solvents and clean-burning, high performance fuels, it is highly desirable to have a process which is more selective for ring opening than currently available. Selectivity for ring opening is related to the propensity for cleavage of a ring bond which results in product molecules having an equivalent number of carbon atoms and one less ring than the original molecule, rather than cleavage of a bond which results in a product molecule having fewer carbons than the original molecule. A perfectly selective ring opening process would give only ring bond cleavage to produce molecules having an equivalent number of carbon atoms and one less ring than the original molecule. For example, from a hydrocarbon stream containing only single ring naphthenes of n number of carbon atoms, the product from perfect ring opening selectivity would be only paraffins of n number of carbon atoms.

Thus, the greater number of product molecules from a ring opening process having an equivalent number of carbon atoms and one less ring than the original molecule, the greater the selectivity for ring opening. Greater selectivity for ring opening is important for the reasons that a) the number of ring structures in a product stream will be decreased, b) significant dealkylation of any pendant substituents on the ring or further cracking of ring opened products which will reduce the volume of product in a specified boiling range, will be minimized and c) the density of the product stream will be decreased providing volume swell. The present invention provides for a ring opening process, and the criteria for selecting a catalyst for that process, with significantly higher selectivity for ring opening than those practiced in the current art, with the object to decrease the number of ring structures in a product stream and decrease the density of the product stream to improve volume swell, while minimizing dealkylation of pendant substituents to maintain a high volume of product in the desired boiling range.

There are a number of references to ring opening in the prior art. Most references fall into two general categories—hydrogenolysis and hydrogenation/hydrocracking. "Hydrogenolysis", for purposes of this invention is defined as cleavage of a molecular bond, with addition of hydrogen at each point of cleavage, of small, single ring naphthenes over primarily noble metal catalysts. "Hydrogenation/hydrocracking" of larger cyclic molecules over primarily acidic zeolite-supported noble and other Group VIII metal catalysts. The more selective ring opening process of the present invention differs in that the catalyst is selected from those which give higher hydrogenolysis activity and selectivity for ring opening than previously recognized or anticipated. Furthermore, they provide significantly less substituent and secondary product cracking in ring opening than observed in conventional hydrocracking processes.

Much academic research has sought to elucidate key mechanisms controlling product distributions in hydrogenolysis and hydrocracking reactions by using model compounds and specific noble metal catalyst types. Typical studies have been reviewed by Gault (Adv. Catal., 30, 1–95, (1981) with a particular attention to $C_6$ ring isomers, including a description of skeletal isomerization of hydrocarbons over metal catalysts and a discussion of the mechanisms of ring opening reactions. The greater ease for ring opening $C_5$ versus $C_6$ cycloparaffin rings and mechanistic implications related to which bond in the $C_5$ ring is cleaved are described.

The isomerization of $C_6$ ring (cyclohexane) to $C_5$ ring (methylcyclopentane) was recognized as a step preceding ring opening (the pentyl-ring opening much faster than the hexyl-ring) was demonstrated by Schultz and co-workers (Proc. 5th Intl. Catal. Congr., North-Holland Publ. (Aidam), v.2, 1229–39, (1973)). The tendency for side chains on ring structures to fragment and isomerize methyl groups to other ring sites (the so called "paring" reaction) has also been demonstrated (Egan, et al, J. Amer, Chem. Soc., 84, 1204–12, (1962). The latter process, which results in tertiary carbon atoms on the ring, severely inhibits ring opening at those sites and is in agreement with the findings of Gault. These processes are characteristic of those using a wide range of metal hydrogenation-acidic catalysts. For instance, various Pt-cation exchanged acidic zeolites have been demonstrated to be effective for isomerizations using cycloparaffins with short side chains (Weitkamp, et al, in "Structure and Reactivity of Modified Zeolites", Elsevier (Aidam), 279–90, (1984)), and are well demonstrated on non-noble metal, non-zeolite catalysts (NiS on amorphous silica-alumina) for longer side-chain $C_9$ to $C_{12}$ alkyl-cyclonapthenes (Egan et al, ibid.) (Egan, et al, J. Amer. Chem. Soc., 84, 1204–12 (1962)). To meet distillate quality targets, control of the paring isomerizations are particularly important in order to limit the number of lower cetane, highly branched paraffins which may result following ring opening.

Other references to ring opening include U.S. Pat. No. 3,617,511 which teaches a catalyst comprised of rhodium or ruthenium on an acidic refractory oxide, specifically a halogen-promoted alumina, for ring opening of cycloparaffins. Greater selectivity for ring opening methylcyclopentane (MCP) versus cyclohexane (CHx) in admixture was observed. In addition, essentially sulfur free feeds were preferred.

Further, U.S. Pat. Nos. 4,783,575 and 4,834,866 disclose the use of a chlorided platinum-alumina catalyst to isomerize $C_4$–$C_6$ paraffins to more highly branched isomers and to ring open cycloparaffins found in the feedstock. Continuous addition of chloride to maintain catalyst acidity and low severity conditions to minimize cracking were preferred. Platinum was found to be most suitable of the catalytic metals.

Also, U.S. Pat. No. 3,631,117 describes a process for the hydroisomerization of cyclic hydrocarbons, specifically isomerization of $C_6$ ring cycloparaffins to $C_5$ ring isomers, employing a zeolite-supported Group VIII metal catalyst for hydroisomerization of cyclics. A broad range of Group VIII metals alone or in combination with each other or with tungsten are claimed. Notably, iridium was absent from this group. The conditions for this hydroisomerization process also provided some ring opening and paraffin isomerization. A note of caution was made that excessive hydrocracking (reducing the number of carbon atoms in the original cyclic molecule) can be a problem under the conditions of $C_6$ ring to $C_5$ ring hydroisomerization.

The sensitivity for cracking of a n-butyl side chain from a $C_5$ ring with platinum on carbon catalysts has been noted (Sergienko, et al., Khim. Geol, Nauk 2, 65–70 (1976)). At relatively mild conditions (225° C. to 270° C.) low yields of $C_9$ paraffins were produced with good selectivity. However, as conversion increased, through either higher platinum loadings or higher temperature, significant amounts of hydrocracking and aromatic products were formed.

There are also patents which teach ring opening in naphtha feeds. For example, of U.S. Pat. No. 5,334,792 discloses a two stage process wherein a naphtha feedstock is reacted in a first stage with a zeolite catalyst containing a hydrogenation component under conditions which will saturate aromatics, such as benzene, and open cyclic hydrocarbons. The reaction product from the first stage is passed to a second stage containing an isomerization catalyst to isomerize paraffins to obtain higher octane products. Also, process of U.S. Pat. No. 5,345,026 comprises contacting cyclic hydrocarbons with a catalyst under sufficient ring opening conditions wherein the catalyst is comprised of: (i) a hydrogenation/dehydrogenation component; and (ii) an acid component comprised of a Group IVb metal oxide modified with an oxyanion of a Group VIb metal.

While hydrocracking can reduce the number of ring compounds in the final distillate product with an attendant increase in the cetane number, the yield of product boiling in the distillate range is reduced by excessive cracking to lower boiling products, including gases. One reason for excessive cracking is that paraffins and paraffinic side chains derived from previously ring opened naphthenes, crack more readily than the remaining napthenes. Comparative analyses of distillate boiling range parraffin contents in both hydrocracking feeds and the resulting products suggests that there is little net increase in paraffins, but rather a concentration of such paraffins in the final product because secondary cracking of the opened napthene rings end up in a lower boiling fraction, outside of the distillate range. Thus, the apparent increase in distillate paraffins, and thus improved distillate fuel quality results primarily from a combination of aromatics saturation and a concentration of paraffins in a reduced volume of product within a given boiling range.

Most recent developments in hydrocracking catalysts have focused on matching the hydrogenation of catalytic noble metals with an acid cracking function. The acid function was provided in earlier catalysts by an amorphous alumina or silica-alumina, and more recently by a crystalline zeolite. The metal function is typically provided by Pt and/or Pd, although all noble metals are treated as functionally equivalent in the patent art. The zeolite component is typically a modified Y-type (U.S. Pat. No. 3,130,007), usually derived from a steamed variety designated "ultrastable-Y", or simply US-Y (U.S. Pat. No. 3,449,070). The art comprises numerous combinations of these two "matched" components, most of which were recently reviewed by Ward (Fuel Process. Technol., 35, 55–85 (1993)) who described in detail the manipulation of product slates by changing catalysts. Key differentiating characteristics are in the variable combinations of Pt and Pd (one or both metals, relative loading, dispersion, distribution between zeolite and matrix) and the particular way in which the US-Y has been processed. The latter components are usually defined by low unit cell values, Si/Al ratios, residual exchange cation contents and sometimes pore volumes. The last property is determined by the methods and intensity for dealuminating which determines the distribution of mesopores within the remnant zeolite crystal and the retained crystalline micropore volume. Ward (ibid.) has authoritatively reviewed the many differences in selectivities between the zeolite products of these numerous process variations.

Attempts have been made to increase hydrocracking selectivity via hydrodecyclization. For example, European Patent Application EP0512652 Al describes a "hydrodecyclization" process wherein the distillate fuel is contacted at elevated temperatures with a suitable catalyst in the presence of hydrogen, which catalyst is comprised of one or more Group VIII noble metals on a modified Y-type zeolite support having a unit cell size between 24.20 Å and 24.40 Å and a $SiO_2/Al_2O_3$ molar ratio of 10 to 150. Similarly, European Patent Application EP05 19573 Al teaches a process for reducing cyclic structures similar to the above EP application except that an alkali or alkaline-earth metal is also present. The objective was to improve the cetane number of distillate fuels by opening rings (hydrodecyclization) without excessive cracking. While these two European patent applications suggest that ring opening is taking place, there is no direct evidence in said applications to suggest that selective ring opening is the reason for improved distillate product quality. Based on process conditions and product yields and qualities provided in the examples, it is more likely that the reported increase in distillate boiling range paraffins and improved distillate fuel quality results primarily from a combination of extensive hydrogenation of aromatics and a concentration of paraffins in a reduced volume of product.

This is in agreement with the observations of Mignard, et al., who studied the opening of naphthenic molecules over a platinum on Y zeolite catalyst under hydrocracking conditions ("Catalytic and Hydroprocessing of Petroleum and Distillates," M. Decker (New York), 447–459 (1994)). The reaction pathway for ring opening of cycloparaffins was described as sequential isomerization of $C_6$ to $C_5$ ring, followed by carbon-carbon bond cleavage to give ring opening, followed by rapid cracking via additional carbon-carbon bond cleavage reactions. The results showed cracking propensity increases with increasing carbon number and that ring opened products are highly susceptible to further cracking. The conclusion reached was that ring opening selectivity to minimize cracking is difficult to control. Indeed these authors suggest that the present state of the art is representative of the limits inherent in the competing reactions involved in hydrocracking under the allowable process conditions.

Hydrocracking catalysts are bifunctional in nature, containing both metal and acidic functionalities. Balancing the relative activity function is of major importance in maintaining high productivity and selectivity. State of the art hydrocracking catalysts are generally dominated by an acid component. Acid catalyzed chemistry is initiated by a metal function in such catalysts by generating olefinic intermediates from paraffinic or cycloparaffinic precursors. There is general consensus in the literature that Group VIII metals are essentially equivalent for this purpose. The dominance of the acid function can lead to excessive cracking since primary products arising from ring opening are highly susceptible to acid cracking routes to lower molecular weight products. Thus, the primary focus on improving the performance of these bifunctional hydrocracking catalysts has been on optimizing the acid function. For these reasons, it remains difficult to control excessive cracking even in state of the art catalysts.

To maintain molecular weight of the products and to reduce volume of lower molecular weight fractions, the cleaving of side chains from ring compounds by the acid component needs to be minimized. Recent attempts to control acidity in zeolites include lowering of Si/Al ratio with cation titration of residual acid sites. However, the approach to low acidity catalysts via dealumination of Y-type reaches a point of diminishing returns because excessive processing, such as multiple stream treatments, exchanges and Al extractions, which are needed to achieve the desired materials results in major yield and crystallinity losses. Thus cation exchange is an alternate and simpler way to control acidity (though not as efficient or stable as control of Si/Al). Methods for controlling acidity and included ammonia titration in the process stream to exchange proton sites (PCT WO/92/13045), base exchange with alkali and alkali earth cations (Euro. Pat. Appl. 0,519 573 Al) and re-alumination exchange methods developed by Lutz (Cryst. Res. Technol., 25, 921–6, (1990)) and others (PCT WO/93/25477).

While many prior catalysts and processes have met with some degree of commercial success, none is capable of selectively opening alicyclic rings without substantial cracking. At best, ring opening may occur, but substituent groups on the ring are severed and/or paraffin products are cracked. For example, in the case of a molecule like butylcyclopentane, prior art processes would be more likely to severe the butyl group, or a portion thereof, from the molecule rather than open the cyclopentane ring. Further, all of the prior art catalysts are comprised of metals on conventional supports, such as alumina, and zeolitic materials.

Therefore, there is still a need in the art for a process for opening 5-membered and 6-membered alicyclic rings in a hydrocarbon feedstock without substantially lowering the boiling point of the product stream.

SUMMARY OF THE INVENTION

In accordance with the present invention there is provided a process for selectively opening five and six membered rings of compounds containing said rings without substantial cracking, which process comprises:

contacting a feedstream containing compounds having one or more five membered rings, six membered rings, or both, with one or more transition metal catalysts at a temperature from about 300° C. to about 450° C. and a hydrogen pressure from about 200 psig to about 2000 psig for an effective amount of time, which transition metal catalyst is selected from the group consisting of transition metal carbides, nitrides, oxycarbides, oxynitrides, and oxycarbonitrides, which transition metal is selected from the group consisting of metals from Groups IVa, Va, and VIa of the Periodic Table of the Elements.

In preferred embodiments of the present invention the transition metal catalyst is selected from the group consisting of oxycarbides, oxynitrides, and oxycarbonitrides.

In other preferred embodiments of the present invention the transition metal catalyst is supported on a support material selected from carbons, carbides, refractory oxides, and nitrides.

In yet other preferred embodiments of the present invention the transition metal is selected from Mo and W.

In a preferred embodiment of the present invention a Group VIII noble metal is also present. The Group VIII noble metal is preferably Ir or Ru.

DETAILED DESCRIPTION OF THE INVENTION

The present process is practiced on feedstocks containing compounds having at least one five-membered ring, or at least one six membered ring, or both. Non-limiting examples of suitable five membered ring compounds include methylcyclopentanes, ethylcyclopentanes, propylcyclopentanes, butylcyclopentanes, pentylcyclopentanes, and indane type compounds. Non-limiting examples of suitable six membered ring compounds include methylcyclohexanes, ethylcyclohexanes, propylcyclohexanes, butylcyclohexanes, pentylcyclohexanes, and decalins. Preferred feedstocks which contain such compounds are petroleum streams boiling in the distillate range, which typically also contains multi-ring compounds. Non-limiting examples of such feeds include diesel fuels, jet fuels, and heating oils, which have average boiling points of about 175° C. to about 400° C.

Three terms commonly used in the literature to describe the transformation of naphthenes to paraffins or to naphthenes containing fewer rings, are "hydrogenolysis", "hydrodecyclization", and "ring opening". Hydrogenolysis reactions are those in which there is cleavage of a carbon-carbon bond, with addition of hydrogen at each point of cleavage. Hydrocyclization is more specific in that a cyclic structure is cleaved in a hydrogen environment. Such reactions occur in the hydrocracking of large organic molecules, with formation of fragments that react with hydrogen in the presence of a suitable catalyst and at relatively high temperatures. Such fragments are typically either molecules in which rings have been cleaved, or are alkyl substituents which have been cleaved, or both. This results in products which contain fewer carbon atoms than the original molecule. This of course results in lower boiling products. "Ring opening" can simply be another way to describe hydrodecyclization. However, for purposes of the present invention, selective ring opening means a high propensity for cleavage of a ring bond which results in product molecules having substantially the same number of carbon atoms and one less ring than the original molecule.

The literature regarding the above terms are typically based on two types of experimental data—real feed data, and model compound data. Examples of feeds on which data is reported in the literature include hydrogenated streams containing cyclic structures, such as hydrocracked products, aromatic hydrogenation products, and deasphalted oils. Streams which contain predominantly aromatics need to be hydrogenated first. Experimental data cited in the art for real feeds usually refer to the disappearance of rings in the products of interest for a particular process, or for total liquid product recovered. Because of the lack of appropriate analytical techniques and characterization tools, the reaction pathways and mechanisms leading to the disappearance of rings cannot be clearly identified and quantified. However, it is common that in such reactions that there has been a substantial reduction in boiling point and/or molecular weight of the product. Boiling point reduction and molecular weight reduction are evidence of non-selective ring opening. That is, of alkyl substituents to the ring being cleaved. There is a substantial amount of literature on ring opening of model compounds, but it is typically limited to simple ring compounds having an alkyl group of only one or two carbon atoms. For example, the majority of experimental data is based on the conversion of methylcyclopentane, cyclohexane, and methylcyclohexane. Only a relatively small amount of data are based on the conversion of compounds having longer carbon substituent groups, such as butylcyclohexane, dimethyl- and trimethyl-cyclopentane.

Hydrogenolysis, as described in the present invention, is a key pathway for ring opening. Hydrogenolysis can be essentially be described by the following two reactions: (1) the breaking of endocyclic carbon—carbon bonds; and (2) the breaking of exocyclic carbon—carbon bonds. The breaking of an endocyclic bond, as in ring opening, leads to a paraffin of same carbon number weight for one ring naphthene or an alkylated naphthene of same number of carbon atoms containing one less ring for a multi-ring naphthene. The breaking of an exocyclic carbon—carbon bond, as in dealkylation, results in the loss of an alkyl substituent which produces a decrease of molecular weight by producing two molecules of much lower boiling points.

Recognizing that the two reactions may occur co-currently or consecutively, it becomes necessary to define the concept of selective and non-selective ring opening and dealkylation. That is, selective ring opening without substantial dealkylation of alkyl substituents on the ring, and non-selective ring opening wherein ring opening is accompanied by substantial dealkylation of ring substituents. For that reason, it is necessary for choosing a selective ring opening catalyst to use a model compound such as butylcyclohexane which contains both a ring and a substituent containing a significant number of exocyclic carbon atoms. It is difficult to determine if a catalyst is selective opening the ring with severing the alkyl substituent for cyclic compounds containing a substituent without a significant number of exocyclic carbon atoms, for example, methylcyclohexane. On the other hand, it is relatively easy to determine whether a catalyst is selectively opening the ring and not severing the substituent on compounds, such as butylcyclohexane, which contain a ring substituent having 3 or more carbon atoms.

The instant process will impact the fuel characteristics of these feedstocks by: (i) reducing number of ring structures in the product stream; (ii) avoiding significant dealkylation of any pendant substituents on the ring which reduces the volume of product in a specified boiling range; and (iii) increasing volume swell by lowering the density of the product stream. It is also desirable to produce distillate fuels with cetane numbers in excess of about 40, preferably in excess of about 45, and more preferably in excess of about 50. The cetane number is directly related to the types of molecules that are found in the distillate fuel. For example, the cetane number of molecules within a class (e.g. normal paraffins) increases with the number of carbon atoms in the molecule. Further, molecular classes may be ranked in terms of their cetane number for a specific carbon number: normal paraffins have the highest cetane number, followed by normal olefins, followed by isoparaffins, and followed by monocyclic naphthenes. Aromatic molecules, particularly multi-ring aromatics, have the lowest cetane numbers.

For example, naphthalene has a cetane blending number of about 5–10; tetrahydronaphthalene (tetralin) about 15, decahydronaphthalene (decalin) about 35–38, butylcyclohexane about 58–62, and decane about 72–76. These cetane measurements, made via engine tests in conjunction with work on the present invention, differ somewhat from values reported elsewhere in the literature (see references), however the trend for higher cetane value with increasing ring saturation and ring opening are consistent.

Further, the aromatics content of a distillate stream will vary depending on its source. For example, if the distillate stream is a product fraction from a crude distillation tower, then the stream will be relatively low in aromatics, particularly multi-ring aromatics and have a relatively high cetane number. Distillate streams which are product fractions from a fluid catalytic cracker, on the other hand, have relatively high amounts of aromatics, particularly multi-ring aromatics and consequently have relatively low cetane numbers. It is know by those having ordinary skill in the art that an increase in cetane number and cetane index may correspond to an increase in API gravity. Consequently, it is highly desirable to reduce the number of rings by selective ring opening.

Catalysts used in the practice of the present invention are selected from the group consisting of transition metal carbides, nitrides, oxycarbides, oxynitrides, and oxycarbonitrides, which transition metal is selected from the group consisting of metals from Groups IVa, such as Ti, and Zr; Group Va, such as V, and Nb; and Group VIa, such as Mo, Cr, and W. The most preferred transition metals are Mo and W, more preferably Mo. The Groups referred to are from the Periodic Table of the Elements as provided by Sargent-Welch Scientific Company, Skokie, Ill.; copyrighted 1979, catalog number S-18806. Preferred are the Group VIa metals, particularly Mo. Also preferred are the oxynitrides and oxycarbides, more preferably oxycarbides.

The above mentioned catalysts contain, in their composition, at least one said transition metal, carbon in the case of carbides, and nitrogen in the case of nitrides, with, in addition, oxygen in the case of oxycarbides, oxynitrides, and oxycarbonitrides. Such compositions are interstitial, stable, solid compounds in which carbon, nitrogen, and oxygen occupy interstitial sites in a complex arrangement. They often adopt simple crystal structures with the metal atoms forming lattices of face-centered (fcc), hexagonal close packed (hcp) or simple hexagonal (hex). Oxygen is particularly ubiquitous, and even materials that are nominally pure carbides, nitrides, and carbonitrides may contain substantial amounts of dissolved oxygen. The effect of oxygen is not necessarily passive, its presence dramatically shifts selectivity from cracking (hydrogenolysis) to isomerization products.

Several processes for preparing such carbides, nitrides, oxycarbides, oxynitrides and oxycarbonitrides are known in the art. For example, a method of preparing carbides and nitrides is disclosed in U.S. Pat. No. 5,200,060 which is incorporated herein by reference. The procedure consists of preparing a Group VIa metal oxide precursor and contacting it with a reactant gas flow in a suitable reactor at a specific temperature program. Another catalyst preparation method suitable for preparing catalysts of the present invention is disclosed in U.S. Pat. No. 4,325,842, which is also incorporated herein by reference. The method consists of impregnating a porous, inert support with a solution of hexamolybenum dodecachloride dissolved in an organic solvent, and heating the impregnated support in a non-oxidizing atmosphere to remove the solvent, and subsequently heating to about 1200°–1382° F. (650°–750° C.) in a carbiding gas mixture comprised of hydrogen, and one or more of; a lower alkane, an alkene, carbon monoxide and noble gas.

Another method suitable for preparing catalysts of the present invention can be found in U.S. Pat. No. 4,325,843, which is incorporated herein by reference. The method consists of impregnating an oxide support material with a solution of a tungsten salt which is decomposable upon heating to the oxide, drying the impregnated support to remove the solvent, heating the resulting support in a non-reducing atmosphere at about 840°–1292° F. (450°–700° C.) to convert the tungsten salt to the oxide, heating the resulting support in ammonia at about 1292°–1472° F. (700°–800° C.) to convert the tungsten oxide to the nitride. This nitride material can subsequently be transformed into a carbide by heating at about 1292°–1472° F. (700°–800° C.) in a carbiding gas mixture comprising hydrogen and a lower alkene/alkane or carbon monoxide.

All carbides and nitrides prepared by the previous methods can subsequently be transformed into oxycarbides and oxynitrides by a suitable conventional oxidative treatment.

A preferred transition metal carbide and oxycarbide catalyst preparation method suitable for the use in the present invention is described in patent numbers EP 396,475 and FR 2,657,603, both of which are incorporated herein by reference. According to EP 396,475, carbides of heavy metals are obtained by reacting a transition metal oxide in its solid or gaseous state with a reactive carbon having a large specific surface area (at least equal to 200 $m^2/g$), the carbon quantity generally being in excess, at a temperature between 900° and 1400° C. Any active carbon type is suitable, granulated or agglomerated active carbon being more particularly suitable. This carbon can be previously doped with metallic elements, such as Ce, Ti, U, Zr, Hf, or a lanthanide. More importantly two processes for activating the surface of transition metal carbides are described in U.S. Pat. No 5,139,987 and 5,308,597, both of which are incorporated herein by reference.

The improved activation procedure described in U.S. Pat. No. 5,308,597 resides in dispensing the oxide or oxycarbide layer which temporarily passivates the surface of the carbide when it is brought in contact with the air after synthesis, without any substantial formation of polymeric carbon or complete reduction to the metal. This method is characterized in that the said carbides are impregnated with a dilute solution of a salt of at least one Group VIII noble metal wherein the metal content is between about 0.001 wt. % to 0.05 wt. %.

The activation procedure described in U.S. Pat. No. 5,139,987 is directed to avoid the use of Group VIII noble metals to achieve a high activation level for catalysis of chemical and petrochemical reactions. The conditions of the oxidizing treatment were described as being critical. The oxidizing gas is generally air, but can be pure oxygen or oxygen diluted to a greater or lesser extend by an inert gas. Preference is given to the use of a gas containing at least 10% oxygen. The preferred temperature is between 250° C. and 450° C. In the case of molybdenum carbide with air as the oxidizing gas, the temperature range is more specific and is around 350° C. After an effective amount of time, a stable equilibrium is established on the surface of the catalyst between the disappearance of the oxygen atoms, the diffusion towards the surface of the oxygen atoms from deeper layers and the arrival of reagents. This gives rise to a more or less oxygen-rich carbide phase (oxycarbide), which has a relatively high reactivity for paraffin isomerization.

A preferred preparation method for producing transition metal oxycarbonitrides suitable for the use of the present invention can be found in U.S. Pat. No. 4,418,154, which incorporated herein by reference. The method consists of thermally decomposing an ethylene-diammonium transition metal complex at about 650° C. under an inert gas flow at atmospheric pressure. The resulting pyrophoric material is then passivated by contacting it at room temperature with a gaseous mixture of oxygen and helium.

We have found that such transition metal oxycarbides, oxynitrides and oxycarbonitrides are particularly active catalysts for $C_6$ to $C_5$ naphthene ring isomerization reactions, with minimal molecular weight reduction. Since it is believed that $C_5$ naphthene rings ring-open more readily than $C_6$ naphthene rings over Group VIII noble metals, such as Ir, Pt, (Gault et al., Adv. Catal., 30, 1–95, (1981)) and Ru, such oxy-materials could be used to isomerize $C_6$ rings to $C_5$ rings, followed by opening the $C_5$ rings to the corresponding paraffin with a Group VIII noble metal catalyst. For the purposes of the present invention the Group VIII noble metal can be on the same catalyst particle as the transition metal (the oxycarbide, etc.) catalyst composition or it can be on a separate catalyst particle and used in a mixed bed with the transition metal catalysts. If the Group VIII noble metal is on the same catalyst particle as the transition metal, it is preferred that the transition metal component be on a refractory support, such as silicon carbide or silicon nitride, onto which the Group VIII noble is impregnated. It is preferred that the Group VIII noble metal be selected from Ir, and Ru, more preferably Ir. If it is on the same particle, as soon as the transition metal component isomerizes the $C_6$ ring to a $C_5$ ring a close proximity Group VIII metal provides higher probability of immediately ring opening the newly formed $C_5$ ring.

If the Group VIII noble metal is on a different particle, then a mixed bed of the two types of catalysts can be used wherein one type is the transition metal catalyst and the other type is the Group VIII noble metal, preferably Ir, Ru, or a mixture thereof, on a substantially non-acidic support, such as an alumina. It is to be understood that the first type of catalyst particle, the transition metal material, can also contain Group VIII noble metal as well. The feedstreams can also be treated in a staged process. That is, in a first stage wherein it is contacted with the transition metal type catalyst to cause isomerization of $C_6$ naphthenes to $C_5$ naphthenes, then followed by a second stage wherein the product stream of the first stage, now rich in $C_5$ ring compounds, is contacted with the other type catalyst containing the Group VIII noble mtal(s). One advantage of a staged process is that reaction conditions can be varied from one stage to the other.

Oxycarbide and/or oxynitride and/or oxycarbonitride catalytic materials are also preferred because they retain some of the metallic properties of the parent transition metal carbide or nitride materials and therefore exhibit some of their catalytic properties, such as hydrogenolysis. However, this hydrogenolysis functionality is mitigated in the oxycarbide, oxynitride and oxycarbonitride catalysts by the presence of surface oxygen. The balance of catalytic properties, isomerization and hydrogenolysis, makes the transition metal oxycarbide, oxynitride and oxycarbonitride materials excellent candidates as naphthene and aromatic ring isomerization and ring opening catalysts.

The following examples are presented for illustrative purposes only and should not be taken as being limiting in any way.

EXAMPLE 1

High specific surface area bulk (130 m$^2$/g) molybdenum oxycarbide (Mo$_2$CO$_x$) and silicon carbide supported molybdenum oxycarbide (15% Mo$_2$CO$_x$/SiC) were obtained by the preparation process of example 1 of European application 396,475 and activation procedure described in U.S. Pat. No. 5,139,987. The in-situ reactivating procedure is as follows. The catalyst was heated to 250° C., under standard pure hydrogen flow at 300 psig. Once the temperature was reached, n-heptane was introduced at a liquid hourly space velocity (LHSV) of 1 and a hydrogen treat gas rate (TGR) of 8800 SCF/B/b. The temperature was then increased to 350° C., and the catalyst maintained at those conditions until n-heptane isomerization steady-state activity was reached and maintained for at least 2 hours. The activated molybdenum carbides were then used for naphthene isomerization and ring opening. The products from all the runs were analyzed by on-line and off-line gas chromatography, and product compounds were identified by gas chromatography/mass spectrometry.

For this purpose, 2.2057 g (3 cc) of high surface area activated SiC supported molybdenum oxycarbide, Mo$_2$CO$_x$/SiC was placed in a down flow stainless steel reactor. A series of runs were conducted to illustrate the influence of conversion on methylcyclohexane (MCH) isomerization product selectivity and yield. The runs were made at temperatures ranging from 350° to 400° C., pressures between 200 and 1000 psig, an LHSV between 1 and 2.4, and a hydrogen TGR between 2280 and 5055 SCF/B. The results are shown in FIGS. 1 and 2 hereof.

Figure 1:
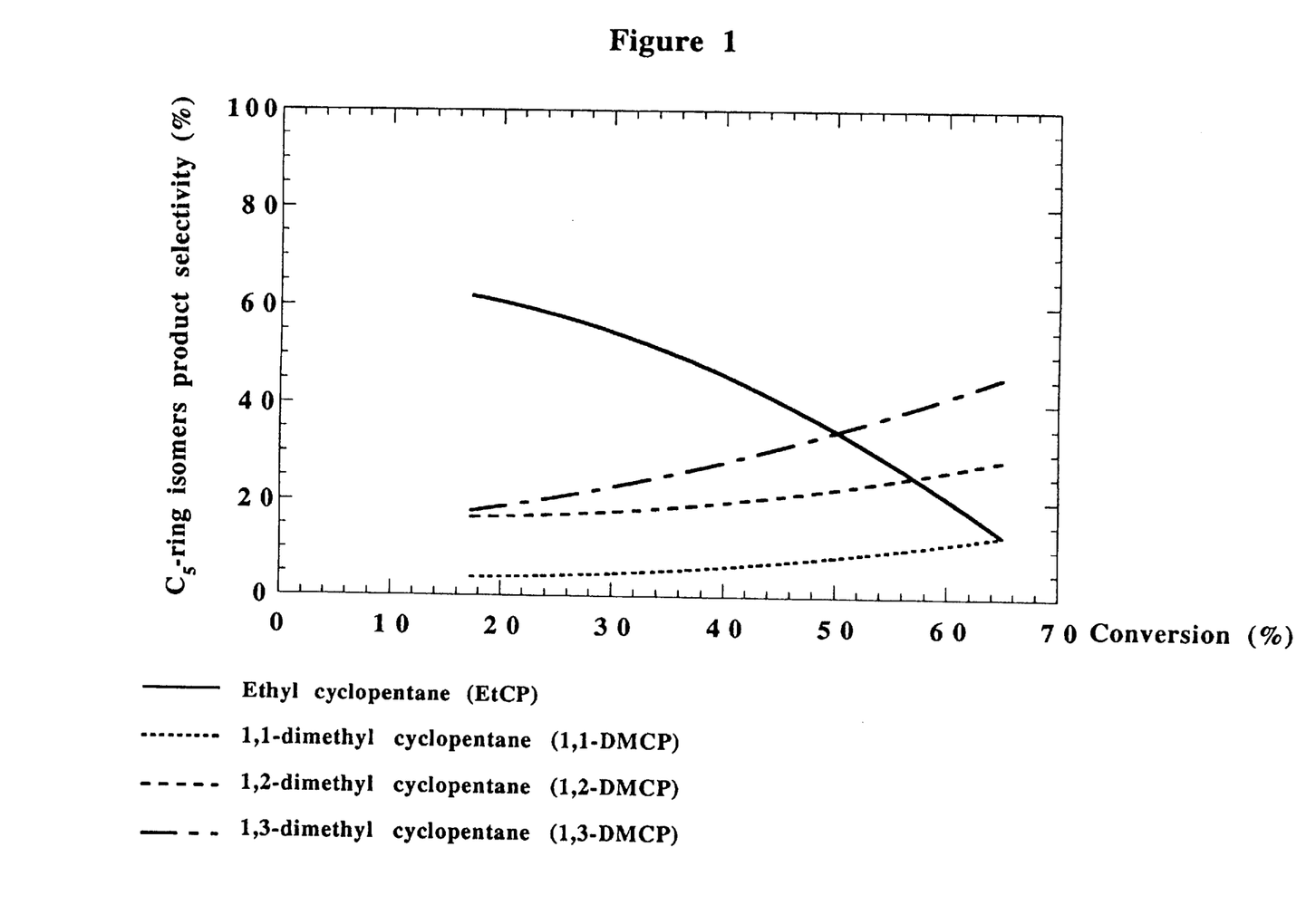
FIG. 1 is a graph representing the $C_5$-ring isomers product selectivity as a function of total methylcyclohexane conversion over $Mo_2CO_x/SiC$.
Figure 2:
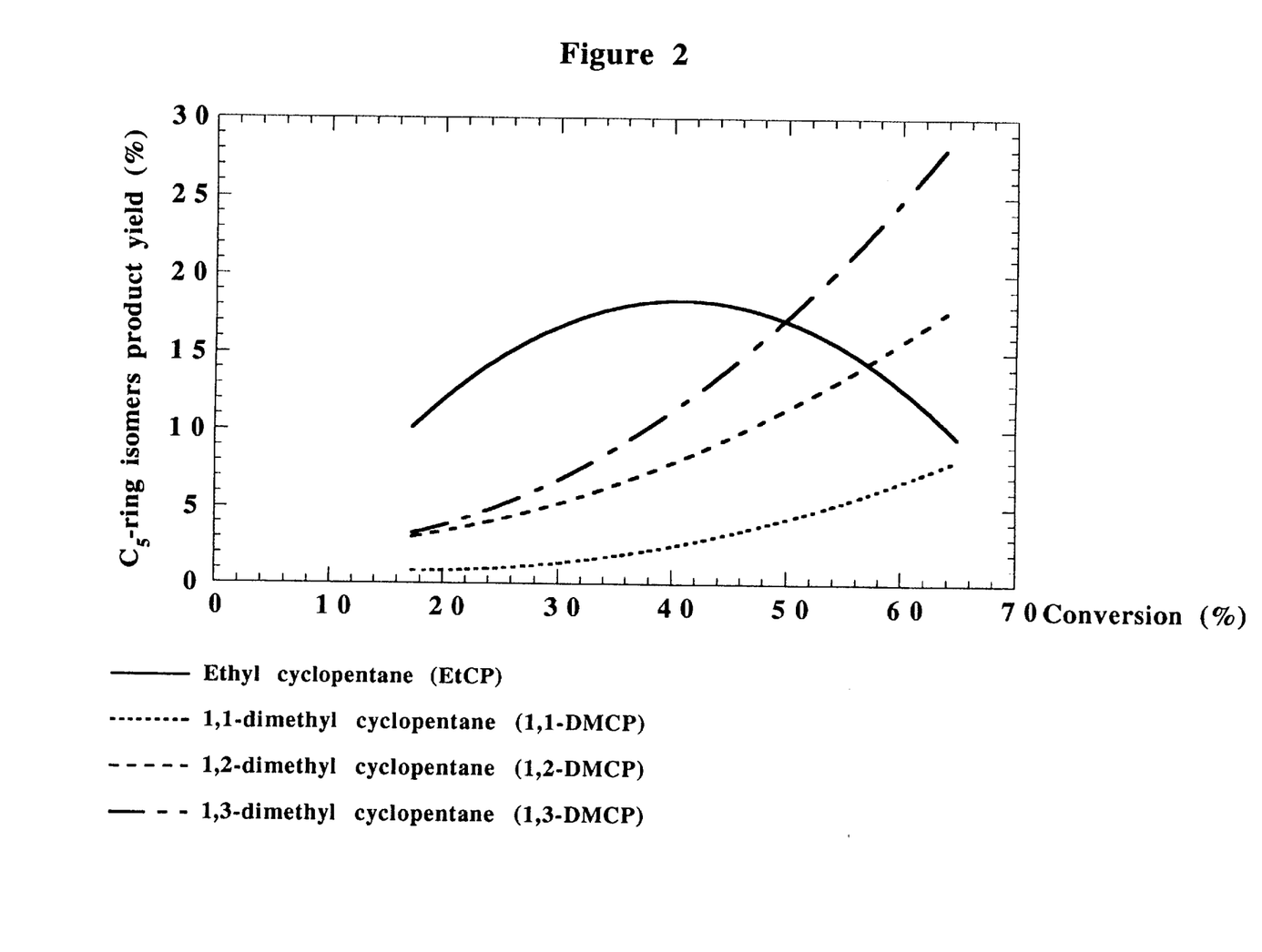
FIG. 2 is graph representing the $C_5$-ring isomers product yield as a function of total methylcyclohexane conversion over $Mo_2CO_x/SiC$.

As is seen in FIG. 1, ethyl cyclopentane (EtCP) selectivity decreases while 1,2- and 1,3-dimethyl cyclopentane (1,2- and 1,3-DMCP) product selectivity increases. The 1,1-dimethyl cyclopentane (1,1-DMCP) product selectivity is maintained low, when increasing MCH conversion. It was found that the naphthene isomerization product selectivity obtained over MO$_2$CO$_x$ is different than that predicted by thermodynamic equilibrium calculation at temperatures between about 350° C. and 400° C., shown in Table I. The data in column A of the table are taken from the paper entitled *Relative Thermodynamic Stability of C7–C8 Cyclopentanes and Cyclohexanes At 295°–600° K.*, by V. A. Zakharenki, et al., *Neftekhimiya*8, No. 5 675–680, 1968. The data in column B are taken from the paper entitled *Selected Values of Physical and Thermodynamic Properties of Hydrocarbon and Related Compounds*, by F. D. Rossini, et al., Carnegy Press, Pittsburgh, 1953. The data in column C are data of this example.

TABLE I

| | Predicted Thermodynamic distribution of various isomers of dimethylcyclopentane. | | |
|---|---|---|---|
| | A<br>$C_5$ Selectivity, % | B<br>Selectivity, % | C<br>Selectivity, % |
| 1,1-MCP | 13.7 | 16.8 | 6 |
| 1,3-MCP | 41.2 | 37.4 | 30 |
| 1,2-MCP | 34.8 | 33.7 | 20 |
| Bt-CP | 11.3 | 12.1 | 44 |
| $C_5$'s-yield | 42% | 42.6% | 42% |
| MCH-yield | 58% | 57.4% | 58% |

In our case, EtCP selectivity is found to be much superior. As is seen in FIG. 2 hereof, EtCP yield reaches a maximum around 40 to 50% MCH conversion.

EXAMPLE 2

Using the same catalyst and apparatus described above in Example 1, a series of runs were conducted using mixtures of 20% alkyl cyclopentane in n-hexane solution. Four runs were made at a temperature of 375° C., a pressure of 500 psig and a hydrogen TGR of 5000 SCF/B. The results are set forth below in Table II.

TABLE II

| | 1,2-DMCP | | 133-DMCP | |
|---|---|---|---|---|
| Total LHSV | 1.67 | 3.33 | 1.67 | 3.33 |
| Conversion (%) | 45.6 | 30.4 | 39.5 | 20.2 |
| Reaction Selectivity (%) | | | | |
| Isomerization($C_5$ rings) | 70.5 | 71.9 | 51.7 | 49.2 |
| Selective Ring opening | 22.5 | 21.7 | 13.7 | 21.6 |
| Ring expansion (MCH) | 5.0 | 3.8 | 32.3 | 26.2 |
| Aromatic | 2.0 | 2.6 | 2.3 | 3.0 |

As is seen, alkyl cyclopentane isomerization is the major reaction. Ring expansion, dialkyl cyclopentane to methyl cyclohexane, is found to be relatively low when using 1,2-DMCP, however, it becomes more significant with 1,3-DMCP. The alkyl cyclopentane ring opening reaction was found in this example to be significant with both model compounds, on the order of at least 20%.

EXAMPLE 3

Figure 3:
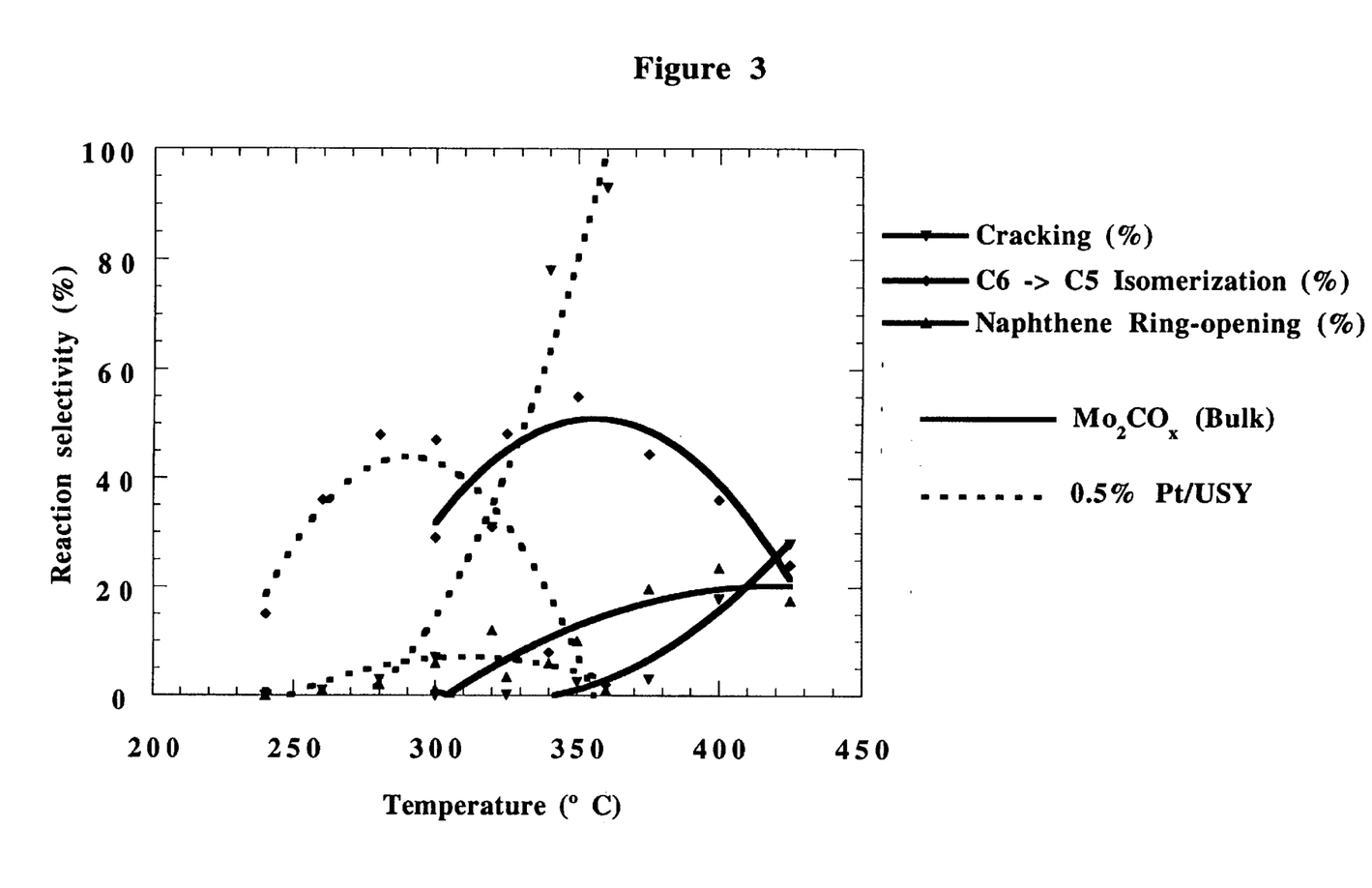
FIG. 3 is a graph comparing an molybdenum oxycarbide reaction selectivity as a function of temperature vs. a 5% Pt/USY hydrocracking catalyst. This data was obtained from Mignard et al., "*Catalytic and Hydroprocessing of Petroleum and Distillates*", M. Decker (New York), 447–459 (1994).

A series of runs were made to determine MCH isomerization and ring opening catalyst activity as a function of operating temperature and pressure for the unsupported high specific surface area molybdenum oxycarbide catalyst ($Mo_2CO_x$), obtained by the preparation process of Example 1. MCH was reacted over bulk molybdenum oxycarbide and the product selectivity was compared with that of a conventional hydrocracking catalyst, 0.5% Pt/USY. The results are shown in FIG. 3 hereof. The comparison is made with data published by Institut Francais du Petrole (IFP) in an unpublished paper given by S. Mignard and N. Marchal, entitled *Opening of Naphthenic Molecules Under Hydrocracking Conditions*, at the April 1994 Spring National Meeting of the American Institute of Chemical Engineers, Atlanta, Ga.

Using the same apparatus and the same general reactivation procedure describe in Example 1, approximately 3.8 cc (5.15 g) of the catalyst was treated before MCH reactivity tests. The operating conditions were: temperatures between 300° and 425° C.; total pressure of 500 psig; LHSV of 1.0; and hydrogen TGR of 8800 SCF/B. The results are shown in Table III.

TABLE III

| Temperature (°C.) | 300 | 325 | 350 | 375 | 400 | 425 |
|---|---|---|---|---|---|---|
| Conversion (%) | 30.2 | 45.9 | 66 | 73.6 | 83.6 | 90.1 |
| Reaction Yield (%) | | | | | | |
| Isomerization | 29.1 | 42.5 | 53.4 | 46.5 | 42.6 | 29.6 |
| SelectiveRing opening | 1.1 | 3.1 | 10.8 | 21.1 | 24.9 | 23.1 |
| Cracking | 0.0 | 0.0 | 0.5 | 1.3 | 2.9 | 14.4 |
| Aromatic | 0.0 | 0.2 | 0.7 | 2.3 | 8.9 | 23.1 |
| Reaction Selectivity (%) | | | | | | |
| Isomerization | 96.2 | 92.6 | 80.9 | 58.4 | 51.0 | 32.9 |
| Selective Ring opening | 3.8 | 6.8 | 16.4 | 25.6 | 29.8 | 25.6 |
| Cracking | 0.0 | 0.0 | 0.7 | 4.2 | 3.5 | 16.0 |
| Aromatic | 0.0 | 0.5 | 1.0 | 3.2 | 10.6 | 25.6 |
| Isomer Selectivity of isomerization products (%) | | | | | | |
| 1,1-DMCP | 9.7 | 11.1 | 11.7 | 11.4 | 11.2 | 12.7 |
| 1,2-DMCP | 24.8 | 26.0 | 33.0 | 32.6 | 32.2 | 28.6 |
| 1,3-DMCP | 36.9 | 40.8 | 39.5 | 39.8 | 40.0 | 42.4 |
| EtCP | 28.6 | 22.1 | 15.8 | 16.2 | 16.6 | 16.3 |
| Selectivity of selective ring open products (%) | | | | | | |
| 2,2-dimethyl pentane | 3.7 | 3.7 | 3.8 | 3.6 | | |
| 2,4-dimethyl pentane | 4.9 | 4.7 | 4.5 | 4.2 | | |
| 3,3-dimethyl pentane | 2.8 | 2.8 | 3.2 | 3.1 | | |
| 2-methyl hexane | 27.7 | 27.6 | 27.0 | 26.8 | | |
| 2,3-dimethyl pentane | 8.8 | 8.5 | 8.5 | 8.3 | | |
| 3-methylhexane | 32.3 | 31.5 | 31.5 | 31.8 | | |
| n-heptane | 19.8 | 21.2 | 21.4 | 22.3 | | |

The results in Table III show that bulk $Mo_2CO_x$ produces high yield of isomerized and ring-opened products and very low cracking when operating below 400° C. The selectivity of isomerized products is found to be constant at all temperatures and close to that of predicted thermodynamic equilibrium calculations. This is different from the results with $Mo_2CO_x$/SiC (Example 1). In the present case the yield of ring opening products is non-negligible and therefore could have an effect on isomerized product selectivity.

EXAMPLE 4

Using the same catalyst, apparatus, and general procedure described in Example 3, a series of runs were conducted to illustrate the influence of the total pressure on reaction selectivity. Four runs were made at a temperature of 375° C.; an LHSV of 1.0; a hydrogen TGR of 8800 SCF/B; and total pressures ranging from 100 to 1000 psig. The results are shown in Table IV.

TABLE IV

| Pressure (psig) | 100 | 300 | 500 | 1000 |
|---|---|---|---|---|
| Conversion (%) | 82.3 | 73.2 | 76.8 | 71.6 |
| Reaction Selectivity (%) | | | | |
| Isomerization | 41.3 | 71.6 | 58.4 | 69.5 |
| SelectiveRing Opening | 3 | 11.3 | 25.6 | 22.9 |
| Cracking | 2.1 | 1.9 | 4.2 | 2.2 |
| Aromatic | 53.4 | 18.7 | 3.2 | 2.2 |
| Isomer Selectivity (%) | | | | |
| 1,1-DMCP | 11.5 | 11.6 | 13.4 | 11.3 |
| 1,2-DMCP | 32.7 | 32.7 | 28.3 | 32.4 |
| 1,3-DMCP | 38.4 | 39.6 | 43.3 | 39.4 |
| EtCP | 17.4 | 16.1 | 15.1 | 16.9 |

The results in Table IV show that decreasing the process total pressure resulted in a slight increase in total conversion. However, a significant change in reaction selectivity was also observed, with MCH dehydrogenation to toluene being the major reaction product.

EXAMPLE 5

Using the same catalyst (bulk $Mo_2CO_x$), apparatus and general procedure described in Example 4, a series of runs were conducted to determine butylcyclohexane (BCH) isomerization and ring opening activity and product selectivity as a function of operating temperature. The results are shown in Table V.

TABLE V

| Temperature (°C.) | 350 | 375 | 400 | 425 |
|---|---|---|---|---|
| Pressure (psig) | 500 | 500 | 500 | 500 |
| LHSV | 1 | 1 | 1 | 1 |
| TGR(SCF/B) | 8800 | 8800 | 8800 | 8800 |
| Liq. Rec. (%) | 95 | 80 | 50 | 40 |
| BCH conversion (%) | 87 | 97.5 | 99.5 | 98 |
| Liquid Product Yield (%) | | | | |

TABLE V-continued

| | | | | |
|---|---|---|---|---|
| $C_{10}$ paraffin | 6 | 24.8 | 15.5 | 7.3 |
| $C_{10}$ Aromatics | 3 | 10.5 | 12 | 9 |
| BCH | 13 | 2.5 | 0.5 | 2.1 |
| $C_{10}$ 1 ring isomers | 76 | 41.8 | 19 | 12.6 |
| $C_{9-}$ (cracked) | 2 | 10.4 | 47 | 69 |
| $C_{10}$ Ring Disappearance (RD) (%) | 12.6 | 48.16 | 81.25 | 90.52 |
| $C_{10}$ R/O selectivity (%) | 47.6 | 51.5 | 19.1 | 8.1 |

Where:

% BCH Conversion=((g BCH in Feed - g BCH in Product)/g BCH in Feed)×100=% BCH Conversion %$C_{10}$ Paraffin Yield (PY)=(g $C_{10}$ Paraffins in Product/g BCH in Feed)×100

%$C_{10}$ Ring Disappearance (RD)=(g BCH in Feed - (g BCH in Product+g $C_{10}$ Cycloparaffins in Product))/ g BCH in Feed)×100

Selectivity for Ring opening (R-O)=(%PY/%RD) % $C_{10}$ Paraffin Yield/%$C_{10}$ Ring Disappearance As is seen, the effect of a longer alkyl group, butyl versus methyl (Example 3), has only little effect on isomerization and ring opening reaction activity and selectivity. It is found that below 400° C. the cracking ($C_{9-}$) is maintained at low levels compared to conventional hydrocracking catalysts (Mignard et al., "*Catalytic and Hydroprocessing of Petroleum and Distillates*", M. Decker (New York), 447–459 (1994)).

EXAMPLE 6

A series of runs were made to determine the effect of the group VIII metal on ring opening activity and selectivity. A bulk high specific surface area molybdenum oxycarbide ($Mo_2CO_x$), obtained by the preparation and activation process of Example 1, was physically mixed with a portion of 0.9 wt. % $Ir/Al_2O_3$ catalyst. $Ir/Al_2O_3$ catalyst was prepared using the following general procedure. The outlet of a large fritted-glass filtration funnel was equipped with a $CO_2$ gas delivery tube allowing the gas to flow upward through the glass frit. Into the funnel were placed 375 ml of de-ionized water and 250 g of reforming grade alumina extrudates. $CO_2$ was bubbled through the mixture for 30 minutes. An Ir stock solution was prepared by the dissolution of 42.9 g of chloroiridic acid hexahydrate in 1 l. of de-ionized water; the stock solution contained 16 mg Ir/ml and 18 mg Cl/ml. To the extrudate/water mixture was added 141 ml of Ir solution, and the passage of $CO_2$ was continued for 4 hours. The aqueous layer was decanted, and the catalyst was dried overnight at room temperature on a bed of paper towels. The catalyst was subsequently dried under vacuum at 100° C. for 4 hours prior to being calcined in flowing air at 400° C. for 3 hours. The finished catalyst contained 0.9 wt. % Ir.

Using the same apparatus and the same general procedure described in Example 1, approximately 5.0 cc (7.1253 g) of bulk $Mo_2CO_x$ and approximately 0.1000 g (0.18 cc) of 0.9 wt. % $Ir/Al_2O_3$ were physically mixed. The total amount of Ir metal in the total catalytic bed is equivalent to 0.012 wt. % or 125 ppm. The operating conditions were as follows: temperatures between 325° and 350° C., total pressures between 500 and 700 psig, LHSV between 0.5 and 2.5, and hydrogen TGR of 3000 SCF/B. The results are tabulated below in Table VI.

TABLE VI

| | | | | | | |
|---|---|---|---|---|---|---|
| Temperature (°C.) | 350 | 350 | 350 | 325 | 325 | 350 |
| Pressure (psig) | 700 | 700 | 500 | 500 | 500 | 500 |
| LHSV | 1 | 2.5 | 2.5 | 0.5 | 1 | 1 |
| TGR(SCF/B) | 3000 | 3000 | 3000 | 3000 | 3000 | 3000 |
| Liq. Rec. (%) | 100 | 93 | 93 | 97 | 95 | 84 |
| BuCH conversion (%) | 76 | 54.2 | 54.2 | 76.2 | 55.4 | 90.3 |
| Liquid Product Yield (%) | | | | | | |
| $C_{10}$ Paraffins | 33.2 | 24 | 21.3 | 34.3 | 21.8 | 33.3 |
| $C_{10}$ Aromatics | 1 | 2 | 3.1 | 0.8 | 1 | 2.5 |
| Butyl cyclohexane | 24.1 | 45.8 | 45.8 | 23.8 | 44.6 | 9.7 |
| $C_{10}$ 1 ring isomers | 24.3 | 20.6 | 20.9 | 29.9 | 25.6 | 30 |
| Cracked $C_{9-}$ | 17.4 | 7.6 | 8.9 | 11 | 7 | 24.5 |
| $C_{10}$ RD (%) | 50.6 | 36.4 | 35.1 | 46.9 | 32.4 | 64.6 |
| $C_{10}$ R/O selectivity (%) | 65.6 | 66.0 | 60.7 | 72.1 | 67.4 | 51.6 |

As is seen, the addition of a small amount of Ir (125 ppm) to the catalytic system dramatically increases the ring opening activity, with the total activity being about equal. It is also observed that increasing the liquid hourly space velocity (LHSV) lowers the cracking ($C_{9-}$) yield without significantly affecting the yield of $C_{10}$ ring opened products or the ring opening selectivity.

What is claimed is:

1. A process for selectively opening five and six membered rings without substantial cracking, which process comprises:

contacting a feedstream containing five membered ring compounds, six membered ring compounds, or mixtures thereof with one or more transition metal catalysts at a temperature from about 300° C. to about 450° C. and a hydrogen pressure from about 200 psig to about 2000 psig, which transition metal catalyst is selected from the group consisting of carbides, nitrides, oxycarbides, oxynitrides, and oxycarbonitrides, of transition metals from Groups IVB, VB, and VIB of the Periodic Table of the Elements, and which transition metal catalyst contains a Group VIII noble metal, and which catalyst will result in at least a 50% selectivity when reacted with butylcyclohexane at a temperature from about 325° C. to 350° C., a pressure from about 500 to 700 psig, a liquid hourly space velocity of 1 to 2.5. and a hydrogen flow rate of 3000 standard cubic feet per barrel, which selectivity is defined as % $C_{10}$ paraffin yield/% $C_{10}$ ring disappearance.

2. The process of claim 1 wherein the transition metal catalyst is selected from the group consisting of oxycarbides, oxynitrides, and oxycarbonitrides.

3. The process of claim 2 wherein the transition metal catalyst is on oxycarbide.

4. The process of claim 1 wherein the transition metal catalyst is supported on a support material selected from carbons, carbides, refractory oxides, and nitrides.

5. The process of claim 4 wherein the support material is silicon carbide.

6. The process of claim 1 wherein the transition metal is selected from Mo and W.

7. The process of claim 6 wherein the transition metal is Mo.

8. The process of claim 2 wherein the transition metal is selected from Mo and W.

9. The process of claim 1 wherein the Group VIII noble metal is selected from the group consisting of Ir, Ru, and Pt.

10. The process of claim 9 wherein the Group VIII noble metal is selected from Ir and Ru.

\* \* \* \* \*